US012485248B2

(12) United States Patent
Dhuper et al.

(10) Patent No.: US 12,485,248 B2
(45) Date of Patent: *Dec. 2, 2025

(54) GAS DELIVERY VENTURI DEVICES

(71) Applicant: AEON RESEARCH AND TECHNOLOGY, INC., Hewlett, NY (US)

(72) Inventors: Sunil Kumar Dhuper, Old Westbury, NY (US); Greg Marler, Rockford, IL (US)

(73) Assignee: AEON RESEARCH AND TECHNOLOGY, INC., Hewlett, NY (US)

( * ) Notice: Subject to any disclaimer, the term of this patent is extended or adjusted under 35 U.S.C. 154(b) by 1096 days.

This patent is subject to a terminal disclaimer.

(21) Appl. No.: 17/140,259

(22) Filed: Jan. 4, 2021

(65) Prior Publication Data

US 2021/0205566 A1 Jul. 8, 2021

Related U.S. Application Data

(60) Provisional application No. 62/956,772, filed on Jan. 3, 2020.

(51) Int. Cl.

*A61M 16/12* (2006.01)
*A61M 16/06* (2006.01)
*A61M 16/08* (2006.01)

(52) U.S. Cl.

CPC ...... *A61M 16/127* (2014.02); *A61M 16/0683* (2013.01); *A61M 16/0816* (2013.01)

(58) Field of Classification Search

CPC .............. A61M 16/0078; A61M 16/06; A61M 16/0683; A61M 16/0816; A61M 16/0833; A61M 16/0875; A61M 16/1045; A61M 16/12; A61M 16/127; A61M 16/14; A61M 16/20; A61M 16/201; A61M 16/208;

(Continued)

(56) References Cited

U.S. PATENT DOCUMENTS 1,640,528 A 8/1927 Bruhn
2,762,368 A * 9/1956 Bloomfield ............. A61F 9/029 D24/110.2

(Continued)

FOREIGN PATENT DOCUMENTS

GB 869626 5/1961
GB 2407043 A * 4/2005 ............ A61M 16/12

*Primary Examiner* — Annette Dixon
(74) *Attorney, Agent, or Firm* — Leason Ellis LLP

(57) ABSTRACT

A gas venturi connector includes a venturi body having an open first end and an opposing second end that includes a gas port for connection to a supplemental gas source. The venturi body includes a first air entrainment window and a second air entrainment window spaced from the first air entrainment window. Each of the first entrainment window and the second air entrainment window has an L-shape. The connector also has a movable shutter that rotates about the venturi body and includes a third air entrainment window and a fourth air entrainment window spaced from the third air entrainment window, wherein registration between the first and third air entrainment windows and the second and fourth air entrainment windows define a degree of air entrainment and the concentration of the supplemental gas delivered to the patient.

15 Claims, 6 Drawing Sheets

(58) Field of Classification Search
CPC ........ A61M 16/209; A61M 2202/0208; A61M 2205/3334; A61M 2205/583
See application file for complete search history.

(56) References Cited

U.S. PATENT DOCUMENTS

| | | | | | |
|---|---|---|---|---|---|
| 3,714,944 | A | | 2/1973 | Price et al. | |
| 3,794,072 | A | * | 2/1974 | Diedrich | A61M 16/12 137/893 |
| 3,850,171 | A | | 11/1974 | Ball et al. | |
| 3,977,432 | A | * | 8/1976 | Vidal | A61M 16/127 137/893 |
| 4,036,253 | A | | 7/1977 | Fegan et al. | |
| 4,043,511 | A | | 8/1977 | Nakamura | |
| 4,400,138 | A | * | 8/1983 | Baer | B01F 25/314 417/195 |
| 4,487,553 | A | * | 12/1984 | Nagata | F04F 5/466 417/171 |
| 4,634,050 | A | * | 1/1987 | Shippee | F25C 3/04 239/10 |
| 4,649,912 | A | * | 3/1987 | Collins | A62B 7/12 128/202.13 |
| 4,848,333 | A | | 7/1989 | Waite | |
| 4,886,055 | A | | 12/1989 | Hoppough | |
| 4,903,897 | A | | 2/1990 | Hayes | |
| 5,372,129 | A | | 12/1994 | Ryder | |
| 5,386,940 | A | | 2/1995 | Berfield | |
| 5,862,543 | A | | 1/1999 | Reynoso et al. | |
| 6,609,518 | B2 | | 8/2003 | Lamb | |
| 7,353,811 | B2 | | 4/2008 | Weisz | |
| 9,289,568 | B2 | | 3/2016 | Dhuper et al. | |
| 10,052,451 | B2 | * | 8/2018 | Dhuper | A61M 16/209 |
| 2002/0092928 | A1 | | 7/2002 | Conroy | |
| 2006/0237559 | A1 | | 10/2006 | Chih | |
| 2010/0032500 | A1 | | 2/2010 | Righini | |
| 2010/0294254 | A1 | | 11/2010 | Ward | |
| 2012/0097170 | A1 | | 4/2012 | Dawson | |
| 2012/0240924 | A1 | | 9/2012 | Rustad | |
| 2012/0312898 | A1 | | 12/2012 | Sesser et al. | |
| 2013/0199535 | A1 | * | 8/2013 | Dhuper | A61M 16/209 128/204.25 |

* cited by examiner

GAS DELIVERY VENTURI DEVICES

CROSS REFERENCE TO RELATED APPLICATION

The present application claims priority to and the benefit of U.S. patent application Ser. No. 62/956,772, filed Jan. 3, 2020, which is hereby incorporated by reference in its entirety.

TECHNICAL FIELD

The present invention relates to medical devices and more particularly, relates to gas delivery venturi devices for controllably delivering a gas to a patient.

BACKGROUND

The venturi effect is the reduction in fluid pressure that results when a fluid flows through a constricted section of pipe. Many hospital patients require a supplementary level of oxygen in the room air they are breathing, rather than pure or near pure oxygen and this can be delivered through a number of devices dependent on the diagnoses, clinical condition of a patient, level of blood oxygenation (hypoxemia), flow requirement and in some instances patient preference. There are also a number of devices available for oxygen delivery in a spontaneously breathing patient, some of the options being low flow nasal cannula, high flow nasal cannula, face mask, venturi mask, non-rebreather mask, oxygen tent, CPAP/BIPAP mask, etc. The venturi mask is especially desirable where highly controlled low concentration is required, especially in patients who are sensitive to high concentration oxygen and are at a risk of carbon dioxide retention when given high concentration oxygen (an example of such patient would be one with the diagnoses of COPD).

The venturi mask, also known as an air-entrainment mask, is a medical device to deliver a known oxygen concentration to patients on controlled oxygen therapy. Venturi devices often use flow rates between 2 and 12 LPM, with a concentration of oxygen delivered to the patient of between 24% and 50%. Venturi masks are considered high-flow oxygen therapy devices. This is because venturi masks are able to provide near total required inspiratory flow at a specified $F_1O_2$ (fraction of inspired oxygen) to a patient's therapy. The kits usually include multiple jets in order to set the desired $F_1O_2$ which are usually color coded. The color of the device reflects the delivered oxygen concentration, for example: blue=24%; yellow=28%; white=31%; green=35%; pink=40%; orange=50%. The color however varies with different brands and the user must check the instructions for use to determine the correct color for the desired $F_1O_2$. A venturi connector can be used and is connected to the patient through a face mask or the like and to a gas source (in this case oxygen) which delivers oxygen to the patient by means of the face mask. The venturi connector has air entrainment openings or ports that draw air into the venturi connector for mixing with the gas (oxygen) that is flowing through the venturi connector to deliver a metered amount of a gas mixture to the patient.

Though venturi masks may accurately deliver a predetermined oxygen concentration to the trachea, generally up to 50%, there could be a greater level of inaccuracy in delivering higher concentration when a patient's flow requirement is high during respiratory distress and a high level of air entrainment happens through the secondary entrainment ports that are mostly a part of the interface mask device. There may be a reasonable level of predictability when considering primary air entrainment from the primary venturi entrainment ports but there is high level of unpredictability when considering the secondary entrainment from the interface mask device entrainment ports. Hence, a patient could be at a risk of developing hypoxemia due to inaccurately delivered low oxygen concentration than stated or predicted. The current venturi devices are therefore fraught with problems and need improvement and better accuracy of predictability.

There are other disadvantages with a venturi system, and that is that there are a large number of parts that are included in the venturi kit, especially multiple venturi connectors and therefore, the kit can be rather bulky and cumbersome. For example, if the oxygen concentration has to be varied, a completely new venturi connector having the proper jet (nozzle) is needed and thus, requires the previous nozzle to be removed and then the new nozzle is connected to the rest of the equipment. In addition, the flow of oxygen has to be adjusted for each venturi connector. This task requires time and moreover, is an interruption to the patient's treatment. In addition, most medical providers other than respiratory therapists are not easily familiar with the intricacies of venturi devices, they are not familiar with venturi principals, they require special training, and as such the devices currently being used are not user friendly. The parts of the kit that are not used, thus must be carefully stored and kept track of and could easily get misplaced which is not common in a hospital setting.

There is therefore a need for an improved venturi gas delivery system.

SUMMARY

In one embodiment, a venturi connector includes a venturi body having an open first end, an opposing second end and an internal gas mixing chamber. The venturi connector has a plurality of windows formed in the venturi body proximate the second end. Each window of the plurality of windows is in fluid communication with the internal gas mixing chamber and is open to atmosphere to allow air to be entrained into the internal gas mixing chamber to form a venturi effect. The venturi connector further includes a plurality of gas ports disposed at the second end. Each gas port has a tubular shape configured for connection to a supplemental gas source and each gas port having a different sized gas port orifice formed therein for controlling and defining a gas concentration of the supplemental gas that is delivered to the patient. Each gas port has a corresponding window located adjacent thereto with an upper edge of each gas port being located below an upper edge of the corresponding window.

In an alternative embodiment, a venturi connector includes a venturi body having an open first end and an opposing second end that includes a gas port for connection to a supplemental gas source. The venturi body includes a first air entrainment window and a second air entrainment window spaced from the first air entrainment window. Each of the first entrainment window and the second air entrainment window has an L-shape. The venturi connector also has a movable shutter that rotates about the venturi body and includes a third air entrainment window and a fourth air entrainment window spaced from the third air entrainment window.

BRIEF DESCRIPTION OF DRAWING FIGURES

DETAILED DESCRIPTION OF CERTAIN EMBODIMENTS

Venturi Connector-Low Concentration

As used herein, the term low concentration refers to a delivery of a gas, in this case oxygen, in a concentration of between 20% to 60% (e.g., between 24% and 60%). As described herein, this type of venturi connector acts as a venturi and thus, oxygen from a gas source (canister) is mixed with entrained air from the atmosphere to produce a mixed gas that is delivered to the patient. The above recited percentages reflect the amount (percentage) of oxygen that is in the mixed gas delivered to the patient.

FIGS. 1-4 illustrate a venturi connector 100 according to one embodiment for use in a venturi gas delivery system. As described above, a venturi gas delivery system includes a patient interface/face mask and the venturi (connector, etc.) that includes a jet (nozzle) having a specific gas flow rate to provide a total inspiratory flow at a specified $F_1O_2$ for patient therapy.

In accordance with the present invention, the venturi connector 100 is constructed to be attached to a gas source (not shown), such as an oxygen gas source, and is also connected to a face mask (not shown) or the like that delivers the inhalation gas to the patient.

The venturi connector 100 is formed of a main venturi connector body 110 that has an open first end 112 and a second end 114.

Figure 2:
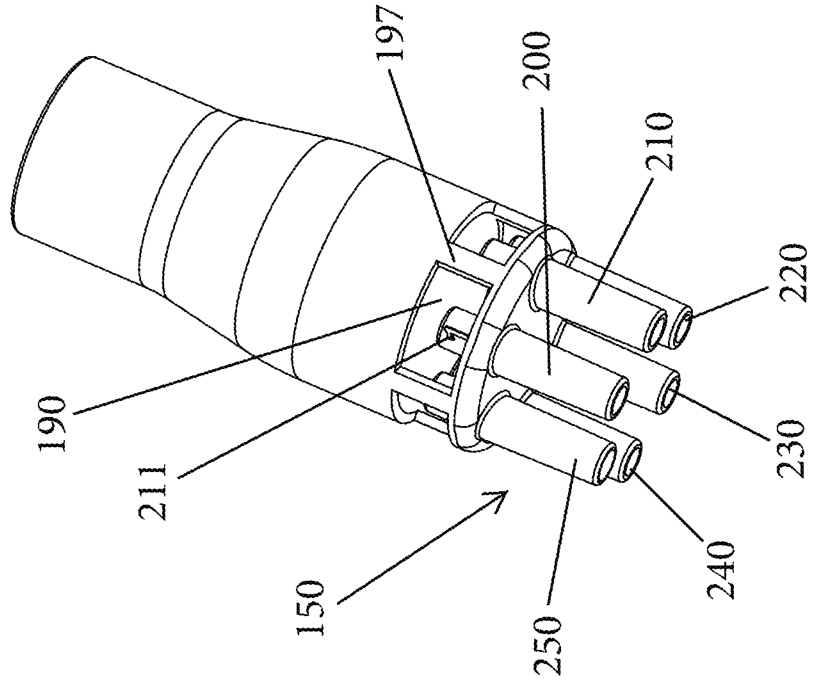
FIG. 2 is a side and bottom perspective view thereof.
Figure 1:
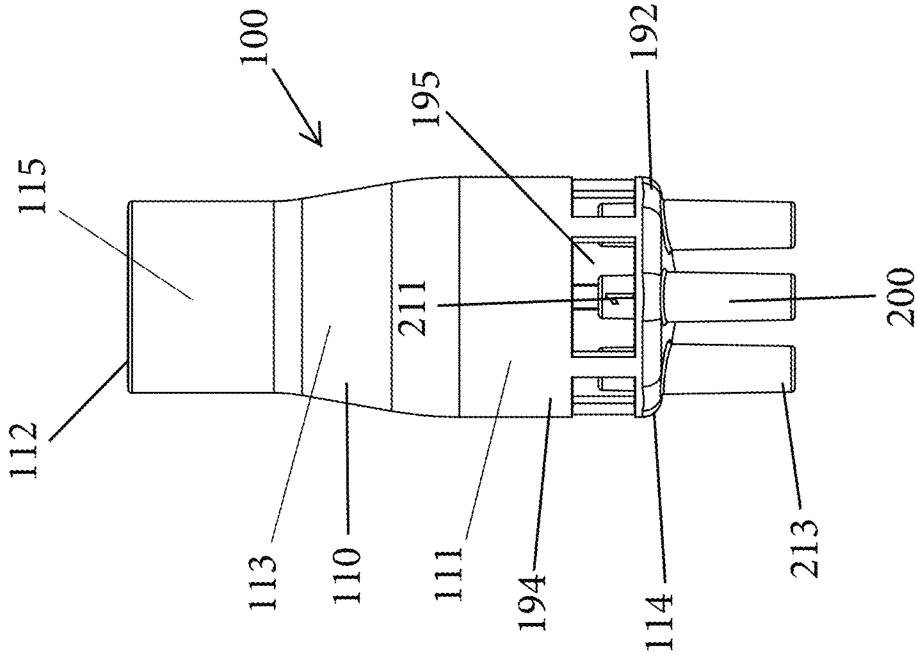
FIG. 1 is a side elevation view of a venturi connector for low gas concentration use.
Figure 4:
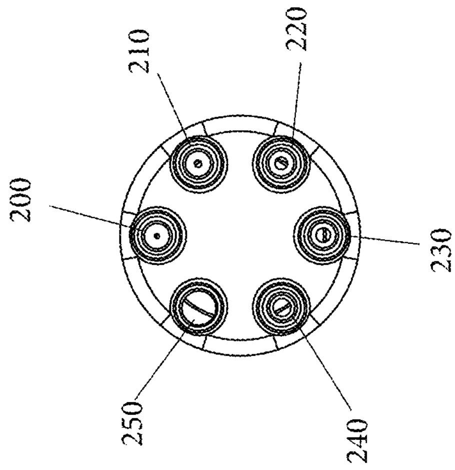
FIG. 4 is a bottom plan view thereof.
Figure 3:
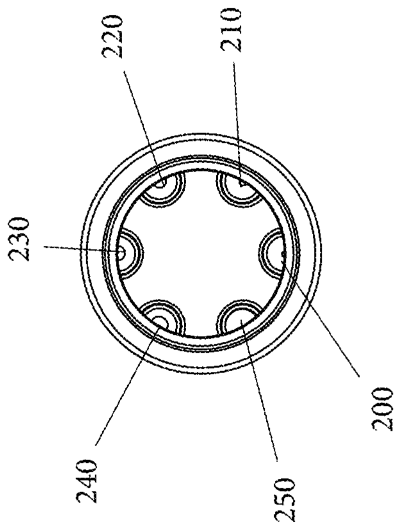
FIG. 3 is a top plan view thereof.
Figure 7:
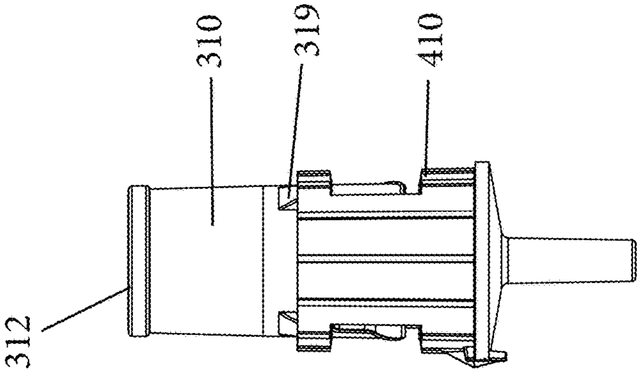
FIG. 7 is a second side elevation view thereof.

As shown, the body 110 has a tapered construction and in particular has an inward taper toward the first end 112 in that a diameter of the body 110 at the first end 112 is less than a diameter of the body 110 at the second end 114. This tapering yields desired gas flow characteristics. More specifically, the body 110 can be thought of as including a bottom portion 111 that has a uniform diameter, a top portion 115 that has a uniform diameter, and an intermediate tapered region 113 that is between the bottom portion 111 and the top portion 115 that has a variable diameter. The diameter of the top portion 115 is less than the diameter of the bottom portion 111. As shown in FIG. 1, the intermediate tapered region 113 comprises a plurality of different tapered sections with each tapered section having a different degree of taper relative to the other tapered sections. These tapered sections as located between the uniform diameter upper and lower portions of the body. In FIG. 1, there are three distinct tapered sections of different degrees of taper as demarcated between horizontal lines in the figure.

By incorporating a taper into the body 110, a higher pressure is maintained in the system since as the mixed gas flows toward the patient interface (mask), the inward taper of the body 110 causes the gas pressure to increase since the gas is being directed into a smaller area (smaller diameter). This increase in pressure maintains velocity of the gas.

In general, the venturi connector 100 is formed of two main components, namely, a multi-port venturi portion 150 and a gas entrainment portion 190. The multi-port venturi portion 150 includes a number of gas ports that permit flow of gas into the venturi connector 100. For example, the gas ports can include a first gas port 200, a second gas port 210, a third gas port 220, a fourth gas port 230, a firth gas port 240 and a sixth gas port 250. The gas ports 200-250 are formed circumferential to one another. Each gas port 200-250 can be in the form of a tubular member that has a first (top) end and a second end 213. The gas ports 200-250 are configured to be individually connected to a gas source (such as an oxygen gas source). As shown in the cross-sectional views of FIGS. 3 and 4, the gas ports 200-250 are elongated hollow conduits that each allows a fluid, such as gas (oxygen), to enter the second end 213 and flow therethrough into the gas entrainment portion 190. Each gas port 200-250 has an associated flow rate and in particular, while the gas ports 200-250 have the same outer diameters, the inner diameter of the gas ports 200-250 differ. In particular, the first gas port 200 is formed with the smallest inner diameter and thus has the least gas flow, while the sixth gas portion 250 is formed with the largest inner diameter and thus, has the greatest gas flow. Each gas port 200-250 can have an identifying indicia 211 formed thereon to help identify the gas port that is to be selected by the user to yield the desired gas flow rate. For example, the indicia can be in the form of numbers such as numbers between 20% and 60% which reflect the concentration of the supplemental gas (oxygen) in the mixed gas breathed by the patient.

The gas entrainment portion 190 has a bottom wall 192 and an upper wall 194 with a hollow gas entrainment section 191 formed in between. In particular, a plurality of air entrainment windows 195 are formed in this region and in the illustrates embodiment, each gas port 200-250 has an associated air entrainment window 195. More particularly, one air entrainment window 195 is located adjacent one gas port 200-250. As shown, the gas port 200-250 can be centrally located within the corresponding air entrainment window 195 which has a rectangular shape.

The gas ports 200-250 can be formed integral to the bottom wall 192 with the top ends of the gas ports 200-250 being located above the bottom wall 192 and within the air entrainment windows 195. With six gas ports 200-250, there are six air entrainment windows 195 with divider walls 197 being formed between the discrete air entrainment windows 195. Each air entrainment window 195 is formed adjacent one discrete gas port 200-250 to allow air inflow (air entrainment) and each air entrainment window 195 can have uniform dimensions.

The air entrainment windows 195 and positioning of the gas ports 200-250 and the hollow space in the hollow gas entrainment section 191 are desired to create a venturi effect in which the gas flow from the gas port into the hollow gas entrainment section 191 while flowing by the air entrainment window 195 which is designed to allow atmospheric gas (air) to be entrained by the gas flow through the gas port.

The distal ends of the gas ports can be barbed ends to facilitate mating of the gas ports to conduits (tubing) that is connected to the same, single gas source or to multiple gas sources.

Venturi Connector—High Concentration

As used herein, the term high concentration refers to a delivery of a gas, in this case oxygen, in a concentration of between 60% to 100%. The above recited percentages reflect the amount (percentage) of oxygen that is in the mixed gas delivered to the patient.

FIGS. 5-9 illustrate a venturi connector 300 according to another embodiment for use in a venturi gas delivery system.

The venturi connector 300 has a valve body 310 with an open first end 312 and a stem 320 with an open second end 324. The stem 320 is configured for attachment to a gas source while the valve body 310 is configured for attachment to a conduit (tube) that leads to a patient interface device, such as a mask. The valve body 310 has a cylindrical shape and the stem 320 also can have a cylindrical shape.

Figure 6:
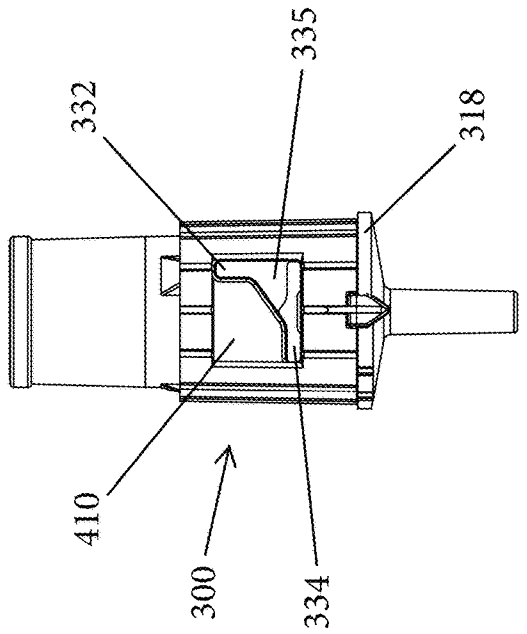
FIG. 6 is a first side elevation view thereof.
Figure 5:
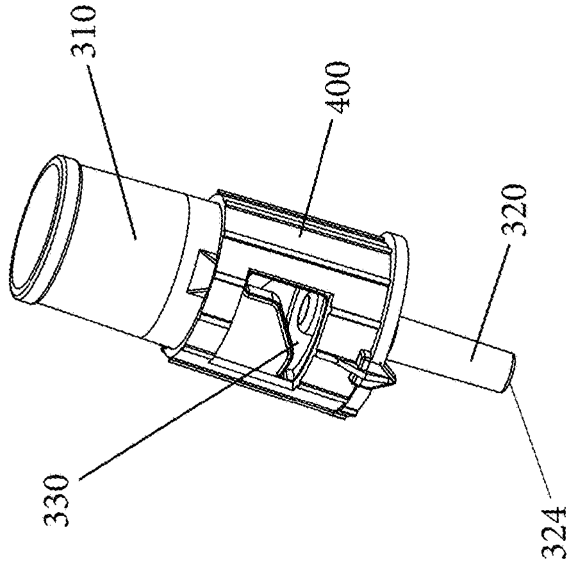
FIG. 5 is a side perspective view of a venturi connector for high gas concentration use.
Figure 9:
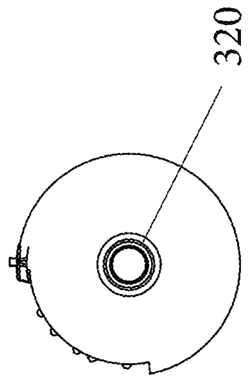
FIG. 9 is a bottom plan view thereof.
Figure 8:
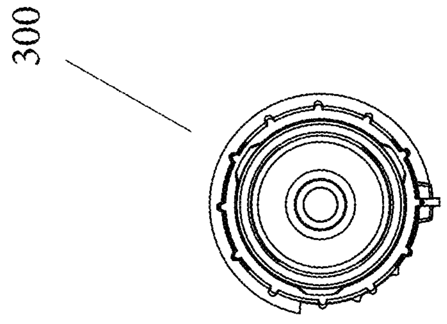
FIG. 8 is a top plan view thereof.

Within the valve body 310 there is one or more air entrainment windows 330 formed therein. For example, as illustrated, there can be two air entrainment windows 330 formed directly 180 degrees apart. Each air entrainment window 330 has an L-shape or dogleg shape as shown in FIG. 6 and is defined by a first leg 332 and a second leg 334 with an intermediate area 335 between the two legs that is open. The air entrainment window 330 is oriented on its side with the first leg 332 pointing upward and the second leg 334 extending horizontal. The ends of the first and second legs 332, 334 represent the smallest open areas of the air entrainment window 330, while the intermediate area 335 represents the largest open area. Together, the first and second legs 332, 334 and intermediate area 335 define the L-shaped opening (window).

The venturi connector 300 includes an actuator 400 that can be in the form of a shutter that is coupled to the valve body 310 and is adjustable relative thereto as by rotating the actuator 400 relative to and about the valve body 310. The actuator 400 is thus disposed around the valve body 310. The actuator 400 includes an air entrainment window 410, in the form of an opening, and in particular, for each air entrainment window 330, there is an associated air entrainment window 410. The degree of registration between the air entrainment window 330 and the air entrainment window 410 determines the degree of air entrainment since atmospheric air can only enter into the venturi when there is overlap (registration) between the air entrainment windows 330 and air entrainment windows 410. By orienting the air entrainment windows 330 directly opposite (180 degrees apart) one another and by having the air entrainment windows 410 directly opposite (180 degrees apart) one another, the degree of registration is the same for each of the two pairs of overlapping air entrainment windows 330, 410.

The actuator 400 can seat on a bottom wall 318 of the valve body 310 and coupling members 319 formed on the valve body 310 can assist in retaining an upper edge of the actuator 400 in place, while still permitting rotation of the actuator.

In FIG. 6, it will be appreciated that the when the air entrainment window 330 and air entrainment window 410 are in full registration, the complete air entrainment window 330 is open as shown. In other words, both first and second legs 332, 334 and the intermediate area 335 are open. As the user rotates the actuator clockwise, one side wall at the end of the air entrainment window 410 begins to cross over and close the first leg 332 and the intermediate area 335 and further clockwise rotation results in the complete intermediate area 335 being closed. Since the intermediate area and first leg 332 represent a large opening, the degree of gas entrainment is significantly reduced. When only the second leg 334 is open, the gas entrainment is low, Finally, if there is no registration, then each air entrainment window 330 is completely closed (since the solid part of the shutter lies thereover) and there is no air entrainment.

The actuator 400, that is adjustable, permits the user to choose from among a plurality of different inspiratory oxygen concentrations depending upon the precise application and the patient's needs.

Figure 10:
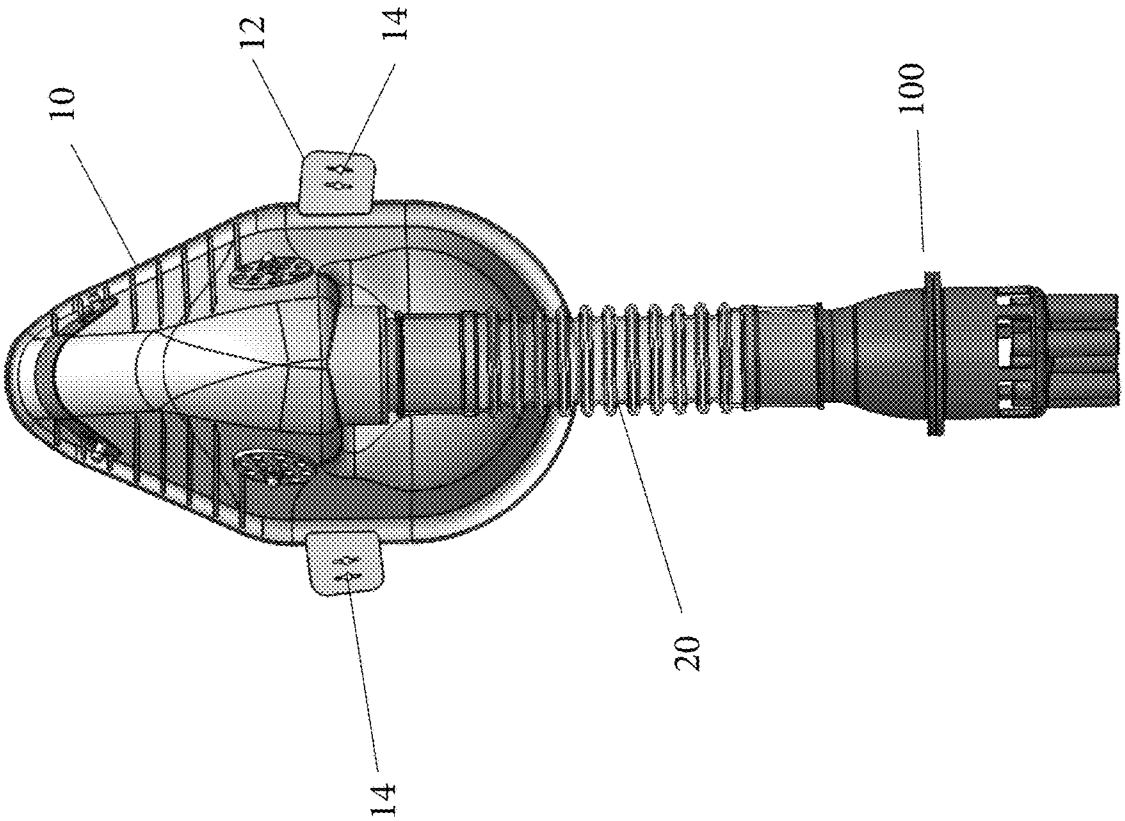
FIG. 10 is a front elevation view of the venturi connector of FIG. 1 coupled to a patient interface device which is in the form of a mask.

FIG. 10 shows an exemplary patient interface 10, such as a face mask, that is worn by the patient. The patient interface 10 can have a pair of side strap attachment tabs 12 that are provided on either side of the patient interface. Each tab 12 has one or more slits 14 for receiving a strap (not shown) that is designed to be fitted about the wearer's head. In accordance with the present application, each slit 14 has a round center opening and two linear end sections. The present applicant has discovered that the inclusion of the round center opening in the slit makes is easier to insert the end of the strap and then subsequently attach the strap to the tab 12.

The patient interface 10 is attached to the venturi connector 100 by a conduit 20 (e.g., traditional tubing). One end of the conduit 20 is attached to an inlet port (e.g., tubular structure) that is part of the patient interface 10, while the other end is attached to the first end 112 of the connector 100.

Figure 11:
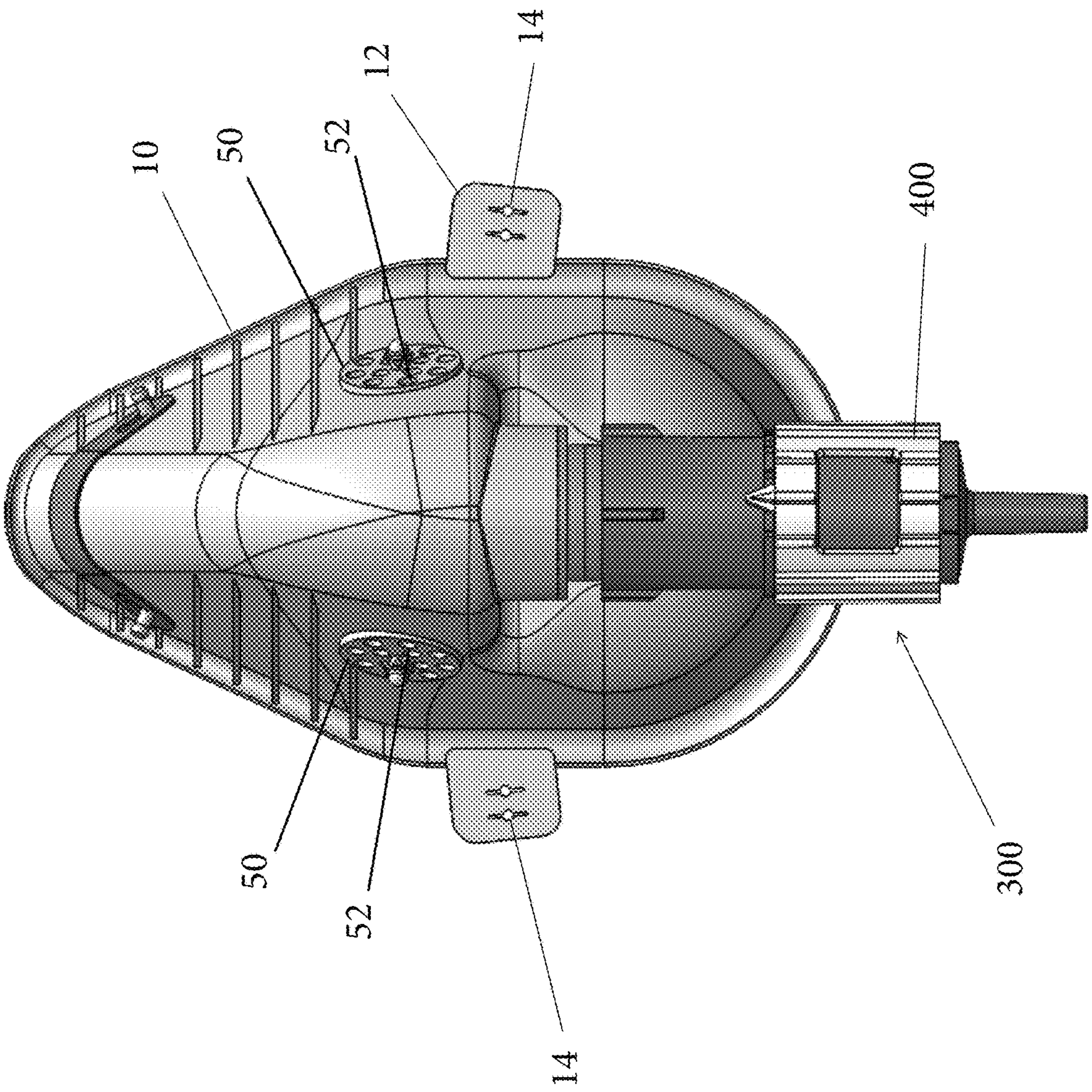
FIG. 11 is a front elevation view of the venturi connector of FIG. 5 coupled to a patient interface device which is in the form of a mask.

FIG. 11 illustrates the venturi connector 300 attached to the patient interface 10 by attaching the first end 312 to the inlet port of the patient interface 10. Unlike in FIG. 10, the embodiment in FIG. 11 does not include the use of the conduit 20.

The patient interface 10 illustrated in FIGS. 10 and 11 also include a feature that is designed to introduce additional breathing gas to the patient. As described below, this feature is a secondary air entrainment feature in which gas (atmospheric air) is entrained with the mixed gas being delivered from one of the venturi connector 100, 300. In one embodiment, the patient interface (mask) 10 has a pair of disks 50 that mounted within openings (not shown) formed in the masks themselves, Each disk (which can have a circular shape) has a plurality of orifices 52 formed therein. The orifices 52 are spaced apart and arranged (e.g., symmetrically) about the disk 50. For example, there can be six orifices 52 located on each half of the disk 50. Since each disk 50 can have 12 orifices 52 in total there can be 24 orifices 52 are designed and intended to allow air to flow through the orifices 52 into the inside of the mask as part of a secondary air entrainment process. The primary air entrainment process occurs at one of the venturi connectors 100, 300 that is connected to the mask. The fast flowing mixed gas from one of the venturi connectors 100, 300 that is entering into the mask causes air to be entrained through these orifices 52.

Alternatively, the orifices 52 are formed directly in the patient interface 10 according to a preselected pattern. For example, the orifices 52 can be die stamped into the patient interface 10 itself such that the orifices 52 represent openings formed directly in the face mask. In this embodiment, there is no discrete air entrainment disk coupled to the face mask but instead, the patient interface 10 can be considered to have a pair of air entrainment areas (regions) in which the orifices 52 are formed (e.g., die stamped) according to the desired orifice pattern (e.g., an arrangement of 12 orifices per air entrainment area). In FIGS. 10 and 11 and according to this embodiment, the reference number 50 identifies the two air entrainment areas on either side of the patient interface 10.

The orifices 52 remain open at all times and are designed so as to not provide increased resistance during respiratory distress. In other words, if the supplemental gas source (e.g., oxygen) were to fail, the orifices 52 allow for a sufficient amount of air to pass through the mask top the patient to maintain satisfactory breathing.

While the dimensions of the human trachea varies depending on gender and patient size, adult tracheas in general have a diameter of at least about 13 mm (0.51 inch) for a small male adult and at least about 10 mm (0.39 inch) for a small adult female. These values are for both the coronal and sagittal diameters. The upper limits of normal for coronal and sagittal diameters, respectively, in men aged 20-79, are 25 mm (0.98 inch) and 27 mm (1.06 inch); in women, they are 21 mm (0.83) and 23 mm (0.91), respectively.

For both male and female adults, the trachea therefore has a cross-sectional area of at least about 0.119 square inches based on a trachea diameter of at least about 10 mm (0.39 inch).

The combined area (sq. inches) of the orifices is at least equal to cross-sectional area of the smallest adult female trachea (based on a 10 mm trachea diameter) such that the patient can breathe through the plurality of orifices 52 (e.g., the 24 orifices formed in the two air entrainment areas of the mask) without any difficulty when there is no air entry from any other port (e.g., a failure of the oxygen source).

In one embodiment, the face mask (i.e., the two air entrainment areas) has a total of twenty-four orifices 52, with twelve orifices 52 on each side of the mask and each orifice has a diameter such that the total collective surface area of the twenty-four orifices 52 is equal to or slightly greater than 0.12 square inches measurement based on the tracheal anatomy as described above. For example, in one embodiment, each 0.08 inch diameter orifice has an area of 0.005 square inches and multiplied by 24 (the number of orifices) is 0.12 square inches (e.g., the target total area of the openings that corresponds to the minimum cross-sectional trachea). To reach at least a combined area of 0.12 square inches, the surface area of each orifice is (0.12 sq inches/24) equal to 0.005 sq. inches and the diameter of the orifice is 0.08 inch. It will be appreciated that is in embodiment, the collective total surface area (sq. inches) of all of the orifices is at least equal to 0.12 sq. inches. It will also be appreciated that this collective total value (0.12 sq inch) is not dependent on the number of orifices. For example, instead of 24 orifices in the above example, the mask can contain 12 orifices in total and in that case, each orifice would have a diameter of 0.16 inch (twice the size as when there were 24 orifices).

In another embodiment, the total collective area of the orifices 52 is at least 0.225 square inches.

The formation of many orifices 52 is in contrast to forming two large openings (mask vents) one on each side of the mask to match that area as larger openings lead to significant entrainment of room air to dilute delivered oxygen concentration especially when the patient is in respiratory distress and the inspiration flow is high. The specifically designed orifices 52 in the mask allow preferential utilization of oxygen delivered by the venturi which in our designed venturi always delivers flow of greater than 15 liters per minute regardless of the port used and there is none to minimal entrainment of room air or ambient air from the orifices 52 in the mask. Had the mask orifices been only two larger openings with one on each side with larger diameter, the flow would have preferentially come from ambient air entrainment diluting the oxygen delivered by the venturi (venturi connectors 100, 300) during respiratory distress when high inspiratory flow is required.

While reducing the diameter of each orifice 52 in the mask, the total area is maintained such that there is no resistance during inspiration or expiration no matter what the flow during patient breathing, calmly or during respiratory distress. Thus, the venturi flow and room air entrainment have been delicately balanced to keep the oxygen delivery concentration within an extremely narrow range regardless of the respiratory condition of the patient without losing any respiratory resistance due to smaller orifice sizes. In addition, these parameters have been delicately balanced to be able to deliver 6 different concentrations of oxygen with the same mask and a single venturi by creating 6 ports (ports 200-250) for oxygen delivery each with a different terminal orifice with a different pressure drop and different ambient air entrainment from the port specific window. The venturi connector 100 has been further tapered at the other end to maintain high velocity (always high flow of greater than 15 liters per min) no matter whether the flow of oxygen to the port is 2 liters or 15 liters.

The venturi connectors 100, 300 disclosed herein are thus constructed to be attached to a gas source (not shown), such as an oxygen gas source, and is also connected to the patient interface 10, which can be in the form of a face mask or the like that delivers the inhalation gas to the patient.

It is to be understood that like numerals in the drawings represent like elements through the several figures, and that not all components and/or steps described and illustrated with reference to the figures are required for all embodiments or arrangements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not precludes the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

What is claimed is:

1. A gas venturi connector comprising:

a venturi body having an open first end, an opposing second end and an internal gas mixing chamber, wherein the venturi body has an outer wall with an outer surface;

a plurality of windows formed in the venturi body proximate the second end, each window of the plurality of windows being in fluid communication with the internal gas mixing chamber and being open to atmosphere to allow air to be entrained into the internal gas mixing chamber to form a venturi effect, wherein each window is defined by a top edge and a bottom edge below the top edge, wherein each window is formed through the outer wall of the venturi body and is open along the outer wall and is open directly to atmosphere, the outer wall comprising an outermost structure of the gas venturi connector; and a plurality of gas ports disposed at the second end, each gas port having a tubular shape configured for connection to a supplemental gas source and each gas port having a different sized gas port orifice formed therein for controlling and defining a gas concentration of the supplemental gas for delivery to a patient; wherein each gas port has a top open end and wherein each gas port has a corresponding window from the plurality of windows located adjacent thereto with the top end of each gas port being located between the top edge and the bottom edge of the corresponding window;

wherein the venturi body has an upper portion that terminates at the open first end and has a first uniform diameter; a lower portion that has a second uniform diameter and an intermediate tapered portion that is located between the upper portion and the lower portion, wherein each of the upper portion, the intermediate tapered portion and the lower portion is located above the plurality of windows;

wherein the intermediate tapered portion is discrete relative to the upper portion and the lower portion and the intermediate tapered portion tapers inwardly in a direction toward the upper portion for delivering the supplemental gas under increased pressure;

wherein the first uniform diameter is less than a diameter of the intermediate tapered portion and is also less than the second uniform diameter, the diameter of the intermediate tapered portion being less than the second uniform diameter.

2. The gas venturi connector of claim 1, wherein the plurality of windows comprises six windows formed circumferentially about the venturi body and the plurality of gas ports comprises six gas ports, wherein between adjacent windows there is a divider wall, each divider wall being disposed between adjacent gas ports.

3. The gas venturi connector of claim 2, wherein each window of the plurality of windows has a rectangular shape, with the top edge of the window being parallel to the bottom edge.

4. The gas venturi connector of claim 2, wherein the six gas ports are spaced circumferentially about the second end and wherein the orifices of the six gas ports are configured to produce gas concentrations of between 20% and 60% of the supplemental gas.

5. The gas venturi connector of claim 2, wherein the six windows are uniform in size with only one respective window being located adjacent one corresponding gas port and wherein and outer diameter of the plurality of gas ports is the same, while an inner diameter thereof varies.

6. The venturi gas delivery system of claim 1, wherein the intermediate tapered portion comprises a plurality of discrete tapered sections with each tapered section having an inward taper toward the upper portion and each tapered section having a different degree of taper relative to the other tapered sections.

7. A venturi gas delivery system comprising:

a patient interface; and the gas venturi connector of claim 1.

8. The venturi gas delivery system of claim 7, wherein the patient interface comprises a mask.

9. The venturi gas delivery system of claim 8, wherein the mask has a pair of strap attachment tabs attached to opposite side edges of the mask, each strap attachment tab having at least one slit formed therein, the at least one slit having a pair of linear ends with a circular center opening.

10. The venturi gas delivery system of claim 8, wherein the mask includes a pair of disks coupled to the mask, each disk have a plurality of orifices formed therein and open to atmospheric air and open into an interior of the mask.

11. The venturi gas delivery system of claim 10, wherein each orifice has a diameter of between 0.08 inch to 0.10 inch.

12. The venturi gas delivery system of claim 10, wherein a total area of the plurality of orifices is at least 0.12 square inches.

13. A venturi gas delivery system comprising:

a patient interface; and the gas venturi connector of claim 1;

wherein the patient interface comprises a mask;

wherein the mask includes a pair of disks coupled to the mask, each disk have a plurality of orifices formed therein and open to atmospheric air and open into an interior of the mask;

wherein one disk is located on one side of the mask and the other disk is on the other side of the mask.

14. A gas venturi connector comprising:

a venturi body having an open first end, an opposing second end and an internal gas mixing chamber, the venturi body having an upper portion that terminates at the open first end and has a first uniform diameter; a lower portion that has a second uniform diameter and an intermediate tapered portion that is located between the upper portion and the lower portion, wherein the second uniform diameter is greater than the first uniform diameter and greater than the intermediate tapered portion and the intermediate tapered portion has an inward taper toward the upper portion, wherein the venturi body has an outer wall with an outer surface;

a plurality of windows formed in the venturi body proximate the second end, each window of the plurality of windows being in fluid communication with the internal gas mixing chamber and being directly open to atmosphere to allow air to be entrained into the internal gas mixing chamber to form a venturi effect, wherein each window is formed through the outer wall of the venturi body and is open along the outer wall; and a plurality of gas ports disposed at the second end, each gas port having a tubular shape configured for connection to a supplemental gas source and each gas port having a different sized gas port orifice formed therein for controlling and defining a gas concentration of the supplemental gas that is delivered to the patient; wherein each gas port has a corresponding window from the plurality of windows located adjacent thereto with an upper edge of each gas port being located below an upper edge of the corresponding window and the each gas port is centrally located with the one corresponding window;

wherein each of the upper portion, the intermediate tapered portion and the lower portion is located above the plurality of windows;

wherein the intermediate tapered portion comprises a plurality of discrete tapered sections with each tapered section having an inward taper toward the upper portion and each tapered section having a different degree of taper relative to the other tapered sections.

15. The gas venturi connector of claim 14, wherein each gas port is located in a middle of the corresponding window as measured along a length of the corresponding window.

* * * * *